United States Patent [19]

Kukes et al.

[11] Patent Number: 4,481,377

[45] Date of Patent: Nov. 6, 1984

[54] DISPROPORTIONATION PROCESS

[75] Inventors: Simon G. Kukes; Robert L. Banks, both of Bartlesville, Okla.

[73] Assignee: Phillips Petroleum Company, Bartlesville, Okla.

[21] Appl. No.: 525,518

[22] Filed: Aug. 22, 1983

[51] Int. Cl.³ .............................................. C07C 3/62
[52] U.S. Cl. .................................... 585/646; 585/647
[58] Field of Search ................................ 585/646, 647

[56] References Cited

U.S. PATENT DOCUMENTS 3,586,731  6/1971  Heckelsberg .
3,676,520  7/1972  Heckelsberg .
3,707,581 12/1972  Heckelsberg .
3,729,525  4/1973  Banks et al. .
4,269,780  5/1981  Benasiak .............................. 585/646

OTHER PUBLICATIONS

Rappe et al, JACS, 104, (1982), pp. 448–456.

*Primary Examiner*—Curtis R. Davis
*Attorney, Agent, or Firm*—Edward L. Bowman

[57] ABSTRACT

A process for the disproportionation of olefins involving the use of a catalyst comprising rhenium oxide and thorium phosphate and oxygen in the feed.

9 Claims, No Drawings

DISPROPORTIONATION PROCESS

BACKGROUND OF INVENTION

This invention relates to the disproportionation of olefin hydrocarbons. In another aspect this invention relates to the use of a rhenium oxide catalyst.

Disproportionation is used herein to denote the conversions of olefin hydrocarbons which can be visualized as comprising the reaction between two first pairs of carbon atoms, the two carbon atoms of each first pair being connected by an olefinic double bond, to form two new pairs from the carbon atoms of said first pairs, the two carbon atoms of each said new pairs being connected by an olefinic double bond. Typical disproportionation reactions include:

(1) The disproportionation of an acyclic mono- or polyene having at least three carbon atoms into other acyclic mono- or polyenes of both higher and lower number of carbon atoms; for example, the disproportionation of propylene yields ethylene and butenes; the disproportionation of 1,5-hexadiene yields ethylene and 1,5,9-decatriene;

(2) The conversion of an acyclic mono- or polyene having three or more carbon atoms and a different acyclic mono- or polyene having three or more carbon atoms to produce different acyclic olefins; for example, the conversion of propylene and isobutylene yields ethylene and isopentene;

(3) The conversion of ethylene and an internal acyclic mono- or polyene having four or more carbon atoms to produce other olefins having a lower number of carbon atoms than that of the acyclic mono- or polyene; for example, the conversion of ethylene and 4-methylpentene-2 yields 3-methylbutene-1 and propylene;

(4) The conversion of ethylene or an acyclic mono- or polyene having three or more carbon atoms and a cyclic polyene to produce an acyclic polyene having a higher number of carbon atoms than that of any of the starting materials; for example, the conversion of cyclohexene and 2-butene yields 2,8-decadiene; the conversion of 1,5-cyclooctadiene and ethylene yields 1,5,9-decatriene;

(5) The conversion of one or more cyclic mono- or cyclic polyenes to produce a cyclic polyene having a higher number of carbon atoms than any of the starting materials; for example, the conversion of cyclopentene yields 1,6-cyclodecadiene;

(6) The conversion of an acyclic polyene having at least seven carbon atoms and having at least five carbon atoms between any two double bonds to produce acyclic and cyclic mono- and polyenes having a lower number of carbon atoms than that of the feed; for example, the conversion of 1,7-octadiene yields cyclohexene and ethylene; or (7) The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

In the prior art there are a number of catalysts for such disproportionation reactions. One type of catalyst comprises rhenium oxide and a support such as alumina, silica, silica-alumina, magnesia-titania, or thorium phosphate. Catalysts comprising rhenium oxide on thorium phosphate support while being interesting have generally been found to have lower activity than some of the other catalysts.

An object of the present invention is to provide a means for increasing the disproportionation activity of a rhenium oxide-thorium phosphate.

SUMMARY OF THE INVENTION

In accordance with the present invention the disproportionation with a catalyst comprising rhenium oxide on a thorium phosphate support is improved by including oxygen in the feed in an amount sufficient to provide an increase in the conversion of at least one of the disproportionable acyclic olefins in said feed.

DETAILED DESCRIPTION OF THE INVENTION

The rhenium oxide/thorium phosphate catalyst can be prepared using any suitable technique known in the prior art.

The thorium phosphate supports can, for example, be readily prepared by combining aqueous solutions of dibasic ammonium phosphate and thorium nitrate, drying at 100°–200° C. overnight, and calcining at 550° C. for two hours in flowing air. Typically such supports will have surface areas in the range of 10 to 150 m$^2$/g.

The amount of Re oxide in the completed catalyst can vary over a wide range, typically, however, it contains from 0.1 to about 30, preferably from 1 to about 15, weight percent of rhenium oxide. A number of rhenium oxides are known in which the valence of rhenium varies from 2 to 7. Consequently, rhenium oxide compositions are likely to be mixtures containing several specific oxides. The most stable oxide is the heptavalent $Re_2O_7$. There is evidence that this compound is the most active for the promotion of olefin disproportionation and is a preferred promoter in the catalyst system of this invention. Therefore, although the other oxides are catalytically active, in general it is preferred to select conditions of catalyst preparation to provide for at least some $Re_2O_7$ to be present in the final catalyst composition.

The composite catalyst is prepared by suitable methods such as dry mixing, impregnation, or coprecipitation. Rhenium oxides or rhenium compounds convertible to an oxide by calcination are employed in the catalyst preparation. A convenient method for the preparation of the catalyst is to dry blend the rhenium oxide and the support in a ball mill where intimate contact between the finely divided particles is achieved. The milled composite can be employed in the process in the finely divided state or can be pressed into pellets or tablets of various sizes and shapes. If desired, pelleted catalysts can be crushed to obtain particles having specific mesh size. Alternatively, a compound of rhenium which is not an oxide can be incorporated into a base following a treatment of the composite to convert the rhenium compound into rhenium oxide.

After the rhenium oxide promoter is associated with the support, the composite is subjected to an activation step before being utilized in the olefin conversion process. The activation technique comprises heating at elevated temperatures in the presence of a suitable flowing gas. Air is a preferred activation gas, although other gases, for example, inert gases such as nitrogen or the noble gases, can be used, provided that at least part of the rhenium present is in the oxide form at the completion of the activation. The catalysts are subjected to a temperature in the range of 700°–1500° F. for 0.5 to 20 hours or longer. Generally, longer activation periods are used with lower temperatures and shorter activation periods with higher temperatures. In some instances, the catalyst is heated serially in more than one gas.

The activated catalyst can be used, without regeneration, for runs of up to several hours or more, and can be regenerated. The regeneration is accomplished by suitable methods for regenerating oxide catalysts and can comprise the same steps used in the activation procedure.

The process of the invention can be carried out either batch-wise or continuously, using a fixed catalyst bed, a stirred batch reactor, a fluidized catalyst bed, or other contacting technique. Preferred reaction conditions, including conditions of temperature, pressure, flow rates, etc., vary somewhat depending upon the specific catalyst composition, the particular feed olefin, desired products, etc. In general, the reaction is carried out in vapor or liquid phase at temperatures from about $-50°$ F. to about 1,200° F., more preferably about 50° to about 250° F., at a pressure of 0–2000 psig.

If desired, paraffinic and/or cycloparaffinic hydrocarbons having up to about 12 carbon atoms per molecule can be employed as diluents for the reaction. Suitable diluents include, for example, propane, cyclohexane, methylcyclohexane, normal pentane, normal hexane, isooctane, dodecane, and the like, or mixtures thereof. The diluents should be non-reacting under the conditions of the disproportionation reaction.

The amount of oxygen needed in the feed to provide an improvement in the conversion is generally very small. Typically the amount of oxygen employed would be in the range of about 0.0001 to about 1 weight percent of the feed, more preferably about 0.05 to 0.5 weight percent of the feed, still more preferably about 0.25 to 0.5 weight percent.

In continuous operation, the optimum range of contact time for this invention process depends primarily upon the activity of the catalyst which is influenced by surface area, promoter concentration, activation temperature, etc., and upon the operating temperature. In general, undesired side reactions are favored by longer contact times. Therefore, the contact time should be maintained as short as possible, consistent with desired conversion.

In general, for continuous operation, weight hourly space velocities in the range of about 0.5 to 1000 parts by weight of hydrocarbon feed per part by weight of catalyst per hour are suitable, with excellent results being obtained in the range of about 1 to 500.

Olefins applicable for use in the process of the invention are acyclic mono- and polyenes having at least 3 carbon atoms per molecule including cycloalkyl and aryl derivatives thereof; cyclic mono- and polyenes having at least 4 carbon atoms per molecule including alkyl and aryl derivatives thereof; mixture of the above olefins; and mixtures of ethylene and the above olefins. Many useful reactions are accomplished with such acyclic olefins having 3–30 carbon atoms per molecule and with such olefins having 4–5 carbon atoms per molecule.

Some specific examples of acyclic olefins suitable for reactions of this invention include propylene, 1-butene, isobutene, 2-butene, 1,3-butadiene, 1-pentene, 2-pentene, isoprene, 1-hexene, 1,4-hexadiene, 2-heptene, 1-octene, 2,5-octadiene, 2,4,6-octatriene, 2-nonene, 1-dodecene, 2-tetradecene, 1-hexadecene, 5,6-dimethyl-2,4-octadiene, 2-methyl-1-butene, 2-methyl-2-butene, 1,3-dodecadiene, 1,3,6-dodecatriene, 3-methyl-1-butene, 1-phenylbutene-2,7,7-diethyl-1,3,5-decatriene, 1,3,5,7,9-octadecapentene, 1,3-eicosadiene, 4-octene, 3-eicosene and 3-heptene, and the like, and mixtures thereof.

Some specific examples of cyclic olefins suitable for the reactions of this invention are cyclobutene, cyclopentene, cyclohexene, 3-methylcyclopentene, 4-ethylcyclohexene, 4-benzylcyclohexene, cyclooctene, 5-n-propylcyclooctene, cyclodecene, cyclododecene, 5,5,4,4-tetramethylcyclononene, 3,4,5,6,7-pentaethylcyclodecene, 1,5-cyclooctadiene, 15,9-cyclodedecatriene, 1,4,7,10-cyclododecatetraene 2-methyl-6-ethylcyclooctadiene-1,4-, and the like, and mixtures thereof.

The advantages of the present invention are illustrated by the following examples.

All runs were made by passing a propylene feed through a vertical tubular quartz reactor (1 cm in diameter and 25 cm in length) positioned in a temperature-controlled electric furnace. In each run the reactor contained a bed of the designated catalyst. A thermocouple was positioned in the catalyst bed to monitor reaction temperature. Prior to each run the catalyst was typically activated by heating at 550° C. in flowing air for 1 hour, followed by flowing nitrogen for 0.25 hours. Regeneration, when indicated, was accomplished with flowing air at 550° C. for up to one hour, followed by a nitrogen flush at about 550° C., then continued nitrogen introduction until the catalyst bed was cooled to the desired reaction temperature.

The propylene feed was of a polymerization grade as sold by Phillips Petroleum Company of Bartlesville, Okla. The propylene feed was pretreated with activated Alcoa H151 alumina and activated magnesia prior to metathesis. The feed was passed downwardly through the vertically oriented tubular reactor. Reaction product analyses were made by gas-liquid chromatography (glc) employing a Hewlett-Packard model 5880A chromatograph having a ⅛ inch by 20 ft. column packed with 19% bis-2-methoxyethoxyethylene (BMEE)+1% squalene on 60/80 Chrom P. Analysis was carried out isothermally at a temperature of about 30° to 40° C. with a helium carrier gas flow rate of about 20 mL/min.

EXAMPLE I

Catalyst Preparations

Control catalyst A ($Re_2O_7.Al_2O_3$) was prepared by adding a solution of 1.8 g. ammonium perrhenate ($NH_4ReO_4$) in 40 mL of water to acid treated alumina support. Harshaw AL-1404 alumina, 20–40 mesh, was acid treated by adding 15 g of alumina to 50 mL of water containing 3 mL of concentrated hydrochloric acid (37% aqueous HCl). The acid suspension of alumina was warmed for 10–15 minutes, liquid decanted, and the treated alumina washed 3×50 mL with distilled water. The treated alumina was dried on a hot plate, then impregnated by addition of the ammonium perrhenate solution, which was evaporated to dryness on the hot plate, then heated to 500° C. for 20 minutes before loading into the reactor.

Control catalyst B ($Re_2O_7.SiO_2$) was prepared by dissolving 1.2 g of ammonium perrhenate in 17.5 mL of distilled water, then pouring the resulting solution over 10 g of Davison silica, 20–40 mesh. The mixture was evaporated to dryness on the hot plate, then heated to 500° C. for 30 minutes before loading into the metathesis reactor.

Control catalyst C (Re$_2$O$_7$.AlPO$_4$) was prepared by adding a solution comprising 1.8 g of ammonium perrhenate dissolved in 30 mL of distilled water containing 5 mL of concentrated ammonium hydroxide (28%) to 10 g of AlPO$_4$. The mixture was warmed on the hot plate until dry, then placed in the metathesis reactor for activation and evaluation with propylene feed.

Control catalyst D (MoO$_3$.Th$_3$PO$_4$)$_4$ was prepared by dissolving 0.22 g of ammonium molybdate in 1.6 mL of water, then adding this solution to 2.25 g of Th$_3$PO$_4$. The mixture was evaporated to dryness on the hot plate, then heated to 500° C. for about 30 minutes before loading into the metathesis reactor for activation and evaluation.

Control catalyst E (Re$_2$O$_7$.ThO$_2$) was prepared by dissolving 2.2 g of ammonium perrhenate in 15 mL of hot water, then adding this solution to 1.4 g of ThO$_2$. The mixture was evaporated to dryness on the hot plate, then loaded into the metathesis reactor for activation and evaluation.

Invention catalyst F(Re$_2$O$_7$.Th$_3$PO$_4$)$_4$, was prepared by adding a solution of 2.7 g ammonium perrhenate in 20 mL of hot water to 15 g of Th$_3$PO$_4$. The mixture was dried on the hot plate, then loaded into the metathesis reactor for activation and evaluation.

EXAMPLE II

The catalysts prepared as described above were evaluated for the self-metathesis of propylene according to the general procedure set forth above. Catalyst employed, reaction conditions employed and reaction results are summarized in the Tables I and II.

TABLE I

| Run | Catalyst, g. | Propylene Flow, mL/min | Cofeed[1], wt. % feed | Temp. °C. | Propylene Conversion, % time on stream, minutes | | | | | | | |
|---|---|---|---|---|---|---|---|---|---|---|---|---|
|  |  |  |  |  | 5 | 25 | 45 | 90 | 120 | 180 | 240 | 300 |
| 1 | A,1.5 | 140 | 0 | 100 | 36.4 | 36.0 | 34.6 | 33.1 | 31.9 | 28.5 | 27.4 | 25.5 |
| 2 | A,1.5 | 140 | 0 | 100 | 36.1 | 34.9 | 33.9 | 32.0 | 30.5 |  |  |  |
|  |  | 140 | A,1.2 | 100 |  |  |  |  |  | 28.2 | 24.6 | 20.6 |
| 3 | A,1.5 | 145 | 0 | 100 | 36.7 | 35.4 | 34.6 | 33.2 | 31.9 |  |  |  |
|  |  |  | A,1.5 | 100 |  |  |  |  |  | 30.8 | 26.2 | 22.1 |
| 4 | B,2.0 | 150 | 0 | 100 | 0.9 |  |  |  |  |  |  |  |
|  |  |  | 0 | 150 |  | 3.3 |  |  |  |  |  |  |
|  |  |  | 0 | 200 |  |  |  | 2.6 |  |  |  |  |
|  |  |  | 0 | 300 |  |  |  |  | 0.4 |  |  |  |
| 5 | B,2.0 | 155 | A,2.0 | 100 | 0.1 |  |  |  |  |  |  |  |
|  |  |  | A,1.4 | 150 |  | 1.1 |  |  |  |  |  |  |
|  |  |  | A,1.5 | 200 |  |  |  | 0.6 |  |  |  |  |
|  |  |  | A,1.6 | 300 |  |  |  |  | 0.2 |  |  |  |
|  |  |  | A,1.2 | 350 |  |  |  |  |  | 0.2 |  |  |
| 6 | C,1.5 | 150 | 0 | 100 | 14.2 | 11.0 | 8.8 | 7.4 | 6.5 | 5.6 | 5.1 | 5.2 |
| 7 | C,1.5 | 140 | 0 | 100 | 17.3 | 11.7 | 9.4 |  |  |  |  |  |
|  |  |  | N,2.0* | 100 |  |  |  |  | 9.0 |  |  |  |
|  |  |  | A,1.5 | 100 |  |  |  |  |  |  | 7.9 | 6.8 |

[1]A = Air, N = Nitrogen
*Nitrogen believed to contain 30 to 100 ppm O$_2$.

TABLE II

| Run | Catalyst, g. | Propylene Flow, mL/min | Cofeed[2], wt. % feed | Temp. °C. | Propylene Conversion, % time on stream, minutes | | | | | | | |
|---|---|---|---|---|---|---|---|---|---|---|---|---|
|  |  |  |  |  | 5 | 25 | 45 | 90 | 120 | 180 | 240 | 300 |
| 8 | D,1.5 | 155 | 0 | 100 | 0.6 | 0.4 |  |  |  |  |  |  |
|  |  |  | 0 | 170 |  |  | 1.2 | 0.7 |  |  |  |  |
|  |  |  | A,1.3 |  |  |  |  |  | 0.1 | 0.03 |  |  |
| 9 | E,3.0 | 145 | 0 | 100 | 0.4 | 0.4 |  |  |  |  |  |  |
|  |  |  | A,1.7 | 100 |  |  | 1.8 |  |  |  |  |  |
| 10 | F,3.0 | 145 | 0 | 100 | 20.4 | 13.7 | 13.8 | 14.2 | 15.1 | 14.8 | 14.2 |  |
|  |  |  | A,1.9 | 100 |  |  |  |  |  |  |  | 24.0 |
| 11 | F,3.0** | 145 | 0 | 100 | 11.8 | 11.8 | 12.2 | 13.1 | 13.5 | 13.4 |  |  |
|  |  |  | A,1.3 | 100 |  |  |  |  |  |  | 19.5 | 15.8 |
| 12 | F,3.0** |  | 0 | 100 | 19.0 | 13.9 | 14.8 |  |  |  |  |  |
|  |  |  | N,1.8*** | 100 |  |  |  | 18.6 | 17.9 | 16.8 |  |  |
|  |  |  | 0 | 100 |  |  |  |  |  | 15.6 |  |  |
|  |  |  | N,2.0*** | 100 |  |  |  |  |  |  |  | 21.4 |
| 13 | F,3.0** | 150 | 0 | 100 | 12.9 | 14.9 | 15.2 |  |  |  |  |  |
|  |  |  | H,0.5**** |  |  |  |  | 16.7 |  |  |  |  |
|  |  |  | N,1.8*** |  |  |  |  |  | 17.7 |  |  |  |
| 14 | F,3.0** | 150 | 0 | 100 | 18.0 | 12.0 | 14.0 | 15.7 | 16.8 | 17.0 |  |  |
|  |  |  | N,1.9*** | 100 |  |  |  |  |  |  | 19.8 |  |
|  |  |  | A,1.2 | 100 |  |  |  |  |  |  |  | 25.7 |

[1]A = Air, N = Nitrogen, H = Helium
**Regenerated catalyst from previous run employed
***Nitrogen Co-feed containing about 30–40 ppm oxygen employed.
****Helium co-feed employed The results of these experiments demonstrate that the addition of oxygen to most metathesis catalysts, such as Re$_2$O$_7$ on alumina, silica or aluminum phosphate support, has no effect or detrimental effect on catalyst activity. A drop in propylene conversion is observed upon addition of oxygen to the propylene feed with catalysts A, B, C and D while a modest increase in propylene conversion is observed upon addition of oxygen to the propylene feed with catalyst E.

Invention runs employing catalyst F demonstrated that even low levels of oxygen added to the propylene feed cause improved conversions.

What is claimed is:

1. In a process for the disproportionation of a feed material comprising at least one disproportionation acyclic olefin having at least 3 carbon atoms per molecule wherein said feed is contacted with a catalyst comprising rhenium oxide on a support comprising thorium phosphate under suitable reaction conditions, the improvement comprising including oxygen in said feed in an amount sufficient to provide an increase in the conversion of at least one of said disproportionable acyclic olefins in said feed.

2. A process according to claim 1 wherein said feed contains about 0.0001 to about 1 weight percent oxygen.

3. A process according to claim 2 wherein said catalyst is prepared by impregnating a thorium phosphate support with an aqueous solution of ammonium perrhenate, then drying, and heating in the presence of oxygen to form rhenium oxide.

4. A process according to claim 3 wherein said feed consists essentially of propylene.

5. A process according to claim 4 wherein the feed contains about 0.25 to about 0.5 weight percent oxygen.

6. In a process for the disproportionation of a feed material comprising at least one disproportionation acyclic olefin having at least 3 carbon atoms per molecule wherein said feed is contacted with a catalyst comprising rhenium oxide on a support comprising thorium phosphate under suitable reaction conditions, the improvement comprising including oxygen in said feed in such an amount that the weight percent oxygen in said feed is in the range of about 0.001 to about 1 weight percent.

7. A process according to claim 6 wherein said feed contains about 0.25 to about 0.5 weight percent oxygen.

8. A process according to claim 7 wherein said catalyst is prepared by impregnating a thorium phosphate support with an aqueous solution of ammonium perrhenate, then drying, and heating in the presence of oxygen to form rhenium oxide.

9. A process according to claim 8 wherein said feed consists essentially of propylene.

* * * * *